United States Patent
Goodwin et al.

(10) Patent No.: US 9,005,971 B2
(45) Date of Patent: *Apr. 14, 2015

(54) GAS SPARGERS AND RELATED CONTAINER SYSTEMS

(71) Applicant: Life Technologies Corporation, Carlsbad, CA (US)

(72) Inventors: Michael E. Goodwin, Logan, UT (US); Nephi D. Jones, Newton, UT (US); Jeremy K. Larsen, Providence, UT (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/094,541

(22) Filed: Dec. 2, 2013

(65) Prior Publication Data

US 2014/0087457 A1  Mar. 27, 2014

Related U.S. Application Data

(63) Continuation of application No. 11/385,541, filed on Mar. 20, 2006, now Pat. No. 8,603,805, which is a continuation-in-part of application No. 11/112,834, filed on Apr. 22, 2005, now Pat. No. 7,384,783.

(51) Int. Cl.
   *C12M 1/04*      (2006.01)
   *B01F 5/04*      (2006.01)
   *B01F 3/04*      (2006.01)
   *B01F 15/00*     (2006.01)
   *C12M 1/00*      (2006.01)

(52) U.S. Cl.
   CPC .............. *B01F 5/04* (2013.01); *B01F 3/04269* (2013.01); *B01F 15/0085* (2013.01); *B01F 2003/04297* (2013.01); *B01F 2003/04326* (2013.01); *B01F 2215/0073* (2013.01); *C12M 23/14* (2013.01); *C12M 23/20* (2013.01); *C12M 29/06* (2013.01)

(58) Field of Classification Search
   None
   See application file for complete search history.

(56) References Cited

U.S. PATENT DOCUMENTS

| | | |
|---|---|---|
| 1,269,189 A | 6/1918 | Kadish |
| 1,471,332 A | 10/1923 | Greenawalt |
| 1,505,204 A | 8/1924 | Kiernan |
| 2,259,243 A | 10/1941 | Daman |
| 2,865,618 A | 12/1958 | Abell |
| 3,184,395 A | 5/1965 | Brewer |
| 3,647,397 A | 3/1972 | Coleman |
| 3,682,168 A | 8/1972 | Deaton |
| 3,796,417 A | 3/1974 | Kaelin |
| 4,012,471 A | 3/1977 | Kunkle, Jr. |
| 4,012,473 A | 3/1977 | Lindsey et al. |
| 4,025,590 A | 5/1977 | Igich |
| 4,036,919 A | 7/1977 | Komendowski et al. |
| 4,061,698 A | 12/1977 | Thornwald |
| 4,100,235 A | 7/1978 | Thornwald |
| 4,204,774 A | 5/1980 | de Bruyne |
| 4,465,645 A | 8/1984 | Kaelin |
| 4,493,637 A | 1/1985 | Ganter et al. |
| 4,668,632 A | 5/1987 | Young et al. |
| 4,684,486 A | 8/1987 | Ricchio |
| 4,727,040 A | 2/1988 | Freedman et al. |
| 4,740,202 A | 4/1988 | Stacey et al. |
| 4,749,654 A | 6/1988 | Karrer et al. |
| 4,814,124 A | 3/1989 | Aoyama et al. |
| 4,869,852 A | 9/1989 | Goudy, Jr. et al. |
| 4,981,623 A | 1/1991 | Ryan |
| 5,008,197 A | 4/1991 | Wergeland et al. |
| 5,057,429 A | 10/1991 | Watanabe et al. |
| 5,183,595 A | 2/1993 | Schüssler |
| RE34,386 E | 9/1993 | Davidson et al. |
| 5,270,207 A | 12/1993 | Matsumura et al. |
| 5,422,043 A | 6/1995 | Burris |
| 5,458,771 A | 10/1995 | Todd |
| 5,565,015 A | 10/1996 | Kobayashi |
| 5,693,537 A | 12/1997 | Wilson et al. |
| 5,799,830 A | 9/1998 | Carroll et al. |
| 5,858,283 A | 1/1999 | Burris |
| 5,897,997 A | 4/1999 | Louvel |
| 5,941,635 A | 8/1999 | Stewart |
| 6,071,005 A | 6/2000 | Ekambaram et al. |
| 6,083,587 A | 7/2000 | Smith et al. |
| 6,086,574 A | 7/2000 | Carroll et al. |
| 6,117,801 A | 9/2000 | McGinty et al. |

(Continued)

FOREIGN PATENT DOCUMENTS

| | | |
|---|---|---|
| CH | 675368 A5 | 9/1990 |
| DE | 200 07 347 U1 | 8/2000 |

(Continued)

OTHER PUBLICATIONS

U.S. Appl. No. 60/577,143, filed Jun. 4, 2004, Hodge.

(Continued)

*Primary Examiner* — Jim Ketter
(74) *Attorney, Agent, or Firm* — Workman Nydegger

(57) ABSTRACT

A container system includes a bag having of one or more sheets of flexible polymeric material, the bag having an interior surface at least partially bounding a chamber that is adapted to hold a fluid. A sparger is secured to the interior surface of the bag so that a compartment is formed between the interior surface of the bag and the sparger. At least a portion of the sparger includes a sparging sheet formed from a flexible sheet of a gas permeable material. A tubular port or tube is coupled with the bag so that a passage bounded by the tubular port or tube communicates with the compartment.

22 Claims, 11 Drawing Sheets

(56) References Cited

U.S. PATENT DOCUMENTS

| | | |
|---|---|---|
| 6,186,932 B1 | 2/2001 | Vallot |
| 6,219,871 B1 | 4/2001 | Frederick et al. |
| 6,245,555 B1 | 6/2001 | Curtis |
| 6,250,796 B1 | 6/2001 | Huang |
| H1989 H | 9/2001 | Fell et al. |
| 6,367,783 B1 | 4/2002 | Raftis |
| 6,391,638 B1 | 5/2002 | Shaaltiel |
| 6,398,195 B1 | 6/2002 | Sherman |
| 6,406,005 B1 | 6/2002 | Lawson et al. |
| 6,432,698 B1 | 8/2002 | Gaugler et al. |
| 6,439,756 B1 | 8/2002 | Forschner et al. |
| 6,464,211 B1 | 10/2002 | Downs |
| 6,468,792 B1 | 10/2002 | Bader |
| 6,494,613 B2 | 12/2002 | Terentiev |
| 6,596,521 B1 | 7/2003 | Chang et al. |
| 6,632,658 B1 | 10/2003 | Schoeb |
| 6,649,405 B2 | 11/2003 | Alms et al. |
| 6,673,598 B1 | 1/2004 | Akers et al. |
| 6,709,862 B2 | 3/2004 | Curtis |
| 6,884,866 B2 | 4/2005 | Bronshtein et al. |
| 6,908,223 B2 | 6/2005 | Bibbo et al. |
| 6,923,567 B2 | 8/2005 | Bibbo et al. |
| 7,141,203 B2 | 11/2006 | Way et al. |
| 7,198,255 B2 | 4/2007 | Chiba |
| 7,278,780 B2 | 10/2007 | Goodwin et al. |
| 7,326,355 B2 | 2/2008 | Graetz et al. |
| 7,384,027 B2 | 6/2008 | Terentiev et al. |
| 7,384,783 B2 | 6/2008 | Kunas et al. |
| 7,431,837 B2 | 10/2008 | Cohee et al. |
| 7,469,884 B2 † | 12/2008 | Terentiev |
| 7,629,167 B2 | 12/2009 | Hodge et al. |
| 7,681,867 B2 | 3/2010 | Hu et al. |
| 7,682,067 B2 | 3/2010 | West et al. |
| 8,282,267 B2 | 10/2012 | Castillo et al. |
| 8,603,805 B2 * | 12/2013 | Goodwin et al. .......... 435/296.1 |
| 2002/0063347 A1 | 5/2002 | Lee et al. |
| 2002/0131654 A1 | 9/2002 | Smith et al. |
| 2003/0077466 A1 | 4/2003 | Smith et al. |
| 2003/0119185 A1 | 6/2003 | Berenson et al. |
| 2004/0062140 A1 | 4/2004 | Cadogan et al. |
| 2004/0095842 A1 | 5/2004 | Weetman |
| 2005/0158851 A1 | 7/2005 | Furey |
| 2005/0218075 A1 | 10/2005 | Graetz et al. |
| 2005/0239199 A1 | 10/2005 | Kunas et al. |
| 2005/0272146 A1 | 12/2005 | Hodge et al. |
| 2005/0282269 A1 | 12/2005 | Proulx |
| 2006/0054557 A1 | 3/2006 | Hori et al. |
| 2006/0196501 A1 | 9/2006 | Bibbo et al. |
| 2006/0270036 A1 | 11/2006 | Goodwin et al. |
| 2008/0068920 A1 | 3/2008 | Galliher et al. |
| 2008/0139865 A1 | 6/2008 | Galliher |
| 2008/0293133 A1 | 11/2008 | Reid et al. |
| 2009/0035856 A1 | 2/2009 | Galliher et al. |
| 2010/0078395 A1 | 4/2010 | Shevitz |
| 2010/0174099 A1 | 7/2010 | Behkish et al. |
| 2011/0020922 A1 | 1/2011 | Wuenn et al. |
| 2012/0238011 A1 | 9/2012 | Tuohey et al. |
| 2012/0313267 A1 | 12/2012 | Pradel et al. |

FOREIGN PATENT DOCUMENTS

| | | |
|---|---|---|
| DE | 20 2010 013 812 U1 | 2/2011 |
| EP | 0 343 885 A1 | 11/1989 |
| EP | 1 602 715 A3 | 12/2005 |
| FR | 2 799 138 | 4/2001 |
| GB | 2 202 549 A | 9/1988 |
| JP | 50-119561 | 9/1975 |
| JP | 58-224683 | 12/1983 |
| JP | 61-067476 | 4/1986 |
| JP | 62-160899 | 7/1987 |
| JP | 2-31825 | 2/1990 |
| JP | 02-283274 | 11/1990 |
| JP | 03-010675 | 1/1991 |
| JP | 03-242297 | 10/1991 |
| JP | 05-336957 | 12/1993 |
| JP | 06-153902 | 6/1994 |
| JP | 70-08264 | 1/1995 |
| JP | 07-155170 | 6/1995 |
| JP | 82-24076 | 9/1996 |
| JP | 2007-511230 | 10/1996 |
| JP | 10-099071 | 4/1998 |
| JP | 10-150972 | 9/1998 |
| JP | 10-313718 | 12/1998 |
| JP | 11-502716 | 3/1999 |
| JP | 11-299478 | 11/1999 |
| JP | 2001-258547 | 4/2002 |
| JP | 2002-101867 | 5/2007 |
| RU | 2 220 917 C1 | 1/2004 |
| WO | 96/30497 | 10/1996 |
| WO | 01/25394 | 4/2001 |
| WO | 02/41484 | 5/2002 |
| WO | 2005/068059 | 7/2005 |
| WO | 2005/118771 | 12/2005 |
| WO | 2006/116067 A1 | 11/2006 |
| WO | 2007/134267 A2 | 11/2007 |
| WO | 2008/040568 A1 | 4/2008 |
| WO | 2008/157181 A1 | 12/2008 |
| WO | 2011/025890 A1 | 3/2011 |

OTHER PUBLICATIONS

DuPont Medical Packaging, *Technical Reference Guide for Medical Packaging*, The Miracles of Science, 2002.
Supplementary European Search Report dated Oct. 15, 2012 issued in EP Application No. 06750951.3, filed Apr. 21, 2006.
U.S. Appl. No. 11/385,541, Feb. 26, 2009, Office Action.
U.S. Appl. No. 11/385,541, Sep. 11, 2009, Office Action.
U.S. Appl. No. 11/385,541, Mar. 31, 2010, Office Action.
U.S. Appl. No. 11/385,541, Jul. ,8, 2010, Notice of allowance and issue fee.
U.S. Appl. No. 11/385,541, Aug. 7, 2012, $2^{nd}$ Notice of allowance and issue fee.

\* cited by examiner
† cited by third party

GAS SPARGERS AND RELATED CONTAINER SYSTEMS

CROSS-REFERENCE TO RELATED APPLICATIONS

The present application is a continuation of U.S. patent application Ser. No. 11/385,541, filed Mar. 20, 2006, which is a continuation-in-part of U.S. patent application Ser. No. 11/112,834, filed Apr. 22, 2005, now U.S. Pat. No. 7,384,783, which are incorporated herein by specific reference.

BACKGROUND OF THE INVENTION

1. The Field of the Invention

The present invention relates to gas spargers and container systems that incorporate a gas sparger.

2. The Relevant Technology

Spargers are commonly used in bioreactors for delivering controlled volumes of gas to a growth media containing cells. In part, the gas is used to control the partial pressure of oxygen within the growth media and to control the pH and other perimeters of the growth media so that the conditions are optimal for cell growth. Spargers typically comprise a hollow metal ring having a hose coupled thereto. The ring is formed from a sintered metal so that the ring is porous. The ring is manually positioned at the bottom of a container with the hose extending up through a port at the top of the container. During operation, pressurized gas is delivered to the ring through the hose. The gas then permeates out through the metal ring so as to enter the media in the form of small bubbles. As the bubbles travel up through the media, at least a portion of the gas becomes entrained within the media. Other conventional spargers comprise a section of stainless steel tubing that is bent into a ring with small diameter holes positioned along the curved length thereof.

Although conventional spargers are useful in delivering gas to the media, they have a number of shortcomings. For example, conventional spargers are relatively expensive to make and are thus designed to be reused. Reuse of a conventional sparger, however, requires that it be removed from the container and then cleaned and sterilized. In some situations, cleaning of the sparger can be difficult in that cell by-product, dead cells, and other particulate within the growth media can be lodged on or trapped within the sparger. Thus cleaning and sterilizing of the sparger can be both time consuming and expensive. Time and care must also be taken to properly position and seal the sparger within the container without contaminating the sparger or the container.

Furthermore, in conventional bioreactors it is necessary that the growth media containing the cells be continually mixed or suspended so that the properties of the growth media remain homogeneous. Conventional spargers can obstruct the flow of the fluid which can produce dead spots where the cells die. Furthermore, the cells can be caught on or by the sparger which can damage or kill the cells. In addition, the spargers must be carefully designed and positioned so that they do not obstruct the mixing system.

Accordingly, what is needed are spargers and container systems that do not require cleaning or sterilization, which can be used without risk of contamination of the container or sparger, and which produce minimum obstruction to the fluid flow within the container and the mixing system.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
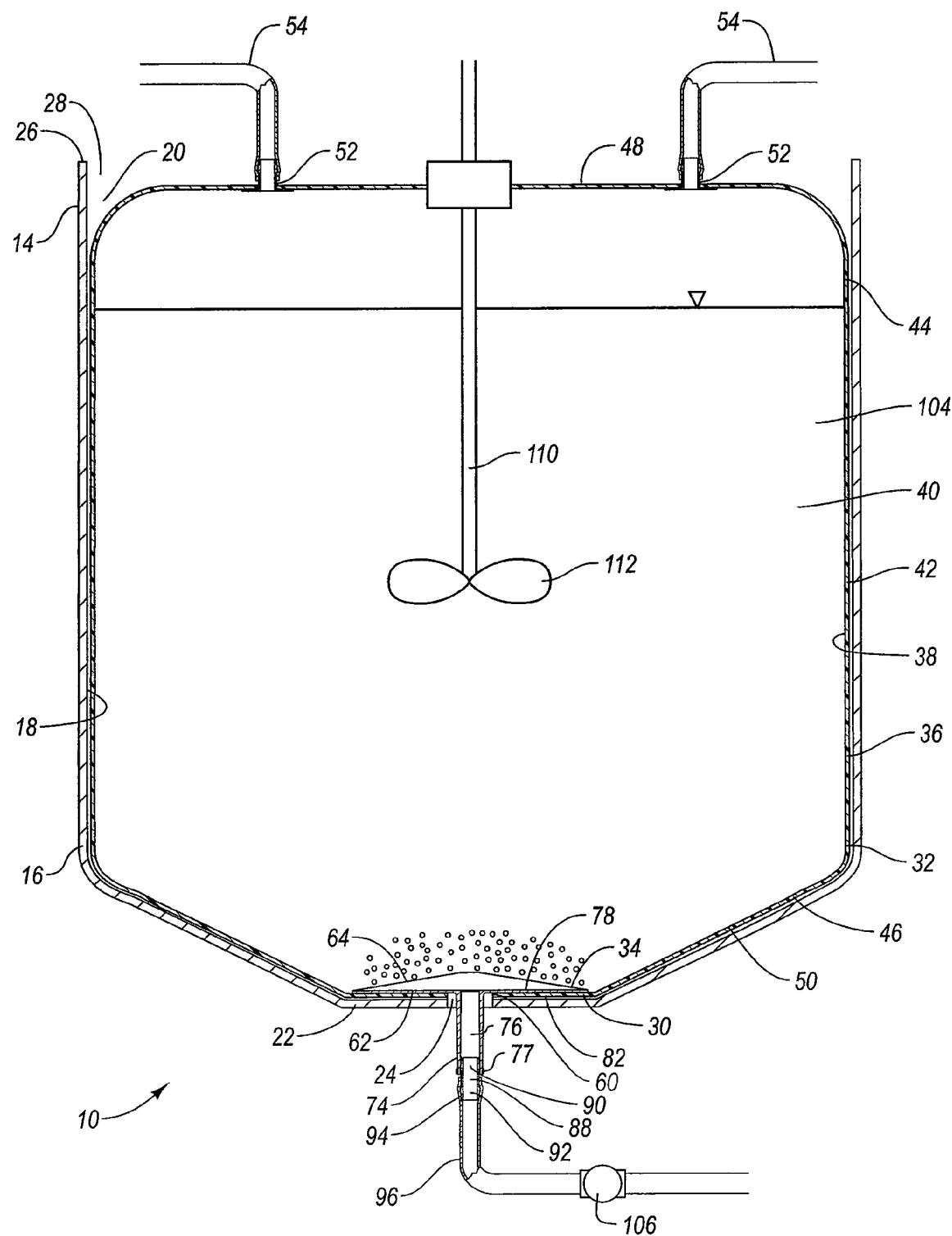
FIG. 1 is a cross sectional side view of a containment system having a sparger.

The present invention relates to gas spargers and container systems that incorporate a gas sparger. In general, the gas spargers of the present invention include a flexible, gas permeable sparging sheet. During operation, a gas is delivered to the sparger which is associated with a container holding a fluid. The gas passes through the flexible, gas permeable sparging sheet of the sparger so as to enter the fluid within the container. As the gas travels or mixes within the fluid, at least a portion of gas becomes entrained within the fluid. The sparger is thus used to control the partial pressure of the gas within the fluid and/or control related properties of the fluid, such as the pH. Such spargers can be used in bioreactors where it is necessary to control the oxygen content and other properties of the growth media to facilitate proper growth of cells and microorganisms. However, the spargers can also be used in fermentation systems and in other fluid processing systems where it is needed or desirable to expose a gas to a fluid.

As a result of using a flexible, gas permeable sparging sheet as the sparging mechanism, select embodiments of the inventive spargers have a variety of unique benefits over conventional rigid metal spargers. By way of example and not by limitation, the inventive spargers are relatively inexpensive to make and can thus be disposed of after a single use. As such, there is no need for cleaning or sterilizing between uses. The spargers can be easily scaled for use in small laboratory experiments or large scale commercial production systems. The flexible, gas permeable sparging sheets can be selected and sized to disperse the gas as micro-bubbles having a desired size over a desired area. Such dispersion enables the gas to be more easily entrained into the fluid while minimizing foam production. In addition, select embodiments of the inventive spargers can be formed on or connected to the container so as to form a low profile sparger that has minimal interference with fluid flow or cell movement within the container.

The inventive spargers can be formed as part of a flexible container, such as a disposable bag or liner, or can be coupled to such flexible containers. The sparger and related container can then be simultaneously sterilized and sold as a unitary system. This approach simplifies the sterilization process and eliminates the difficulty of the end user having to manually insert and properly position the sparger within the container without compromising sterility of the container or the sparger. Alternatively, the disposable spargers of the present invention can be designed to be retrofitted into existing rigid containers. Furthermore, in some embodiments the entire sparger or substantial portions thereof can be designed to be soft and flexible so that the combined sparger and container can be folded and/or rolled into a compact shape for storage and/or transport without risk of damage to the sparger or container. Numerous other advantages of different embodiments of the present invention will be discussed below or will be apparent from the following disclosure and appended drawings.

Depicted in FIG. 1 is one embodiment of a containment system 10 incorporating features of the present invention. Containment system 10 comprises a substantially rigid support housing 12 in which a container system 30 is disposed. Support housing 12 has an upper end 14, a lower end 16, and an interior surface 18 that bound a compartment 20.

Formed at lower end 16 is a floor 22. An opening 24 extends through floor 22 so as to communicate with compartment 20. Upper end 14 terminates at a lip 26 that bounds an access opening 28 to compartment 20. If desired, a cover, not shown, can be mounted on upper end 14 so as to cover access opening 28. It is appreciated that support housing 12 can come in a variety of different sizes, shapes, and configurations. For example, in one alternative embodiment access opening 28 can be closed by a permanent top end wall. An access port can be formed at another location on support housing 12 such as the sidewall or floor. The access port can be selectively closed by a door.

As also depicted in FIG. 1, container system 30 is at least partially disposed within compartment 20 of support housing 12. Container system 30 comprises a container 32 having a sparger 34 mounted thereon. In the embodiment depicted container 32 comprises flexible bag-like body 36 having an interior surface 38 that bounds a chamber 40. More specifically, body 36 comprises a side wall 42 that, when body 36 is unfolded, has a substantially circular or polygonal transverse cross section that extends between a first end 44 and an opposing second end 46. First end 44 terminates at a top end wall 48 while second end 46 terminates at a bottom end wall 50.

Body 36 is comprised of a flexible, water impermeable material such as a low-density polyethylene or other polymeric sheets having a thickness in a range between about 0.1 mm to about 5 mm with about 0.2 mm to about 2 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive.

The extruded material comprises a single integral sheet that comprises two or more layers of different materials that can be separated by a contact layer. All of the layers are simultaneously co-extruded. One example of an extruded material that can be used in the present invention is the HyQ CX3-9 film available from HyClone Laboratories, Inc. out of Logan, Utah. The HyQ CX3-9 film is a three-layer, 9 mil cast film produced in a cGMP facility. The outer layer is a polyester elastomer coextruded with an ultra-low density polyethylene product contact layer. Another example of an extruded material that can be used in the present invention is the HyQ CX5-14 cast film also available from HyClone Laboratories, Inc. The HyQ CX5-14 cast film comprises a polyester elastomer outer layer, an ultra-low density polyethylene contact layer, and an EVOH barrier layer disposed therebetween. In still another example, a multi-web film produced from three independent webs of blown film can be used. The two inner webs are each a 4 mil monolayer polyethylene film (which is referred to by HyClone as the HyQ BM1 film) while the outer barrier web is a 5.5 mil thick 6-layer coextrusion film (which is referred to by HyClone as the HyQ BX6 film).

The material is approved for direct contact with living cells and is capable of maintaining a solution sterile. In such an embodiment, the material can also be sterilizable such as by ionizing radiation. Examples of materials that can be used in different situations are disclosed in U.S. Pat. No. 6,083,587 which issued on Jul. 4, 2000 and United States Patent Publication No. US 2003-0077466 A1, published Apr. 24, 2003 which are hereby incorporated by specific reference.

In one embodiment, body 36 comprises a two-dimensional pillow style bag wherein two sheets of material are placed in overlapping relation and the two sheets are bounded together at their peripheries to form internal chamber 40. Alternatively, a single sheet of material can be folded over and seamed around the periphery to form internal chamber 40. In another embodiment, body 36 can be formed from a continuous tubular extrusion of polymeric material that is cut to length and the ends seamed closed.

In still other embodiments, body 36 can comprises a three-dimensional bag that not only has an annular side wall but also a two dimensional top end wall 48 and a two dimensional bottom end wall 50. Three dimensional body 36 comprises a plurality of discrete panels, typically three or more, and more commonly four or six. Each panel is substantially identical and comprises a portion of the side wall, top end wall, and bottom end wall of body 36. Corresponding perimeter edges of each panel are seamed. The seams are typically formed using methods known in the art such as heat energies, RF energies, sonics, or other sealing energies.

In alternative embodiments, the panels can be formed in a variety of different patterns. Further disclosure with regard to one method of manufacturing three-dimensional bags is disclosed in United States Patent Publication No. US 2002-0131654 A1 that was published Sep. 19, 2002 of which the drawings and Detailed Description are hereby incorporated by reference.

It is appreciated that body 36 can be manufactured to have virtually any desired size, shape, and configuration. For example, body 36 can be formed having chamber 40 sized to 10 liters, 30 liters, 100 liters, 250 liters, 500 liters, 750 liters, 1,000 liters, 1,500 liters, 3,000 liters, 5,000 liters, 10,000 liters or other desired volumes. Although body 36 can be any shape, in one embodiment body 36 is specifically configured to be complementary or substantially complementary to compartment 20 of support housing 12.

In any embodiment, however, it is desirable that when body 36 is received within compartment 20, body 36 is uniformly supported by support housing 12. Having at least generally uniform support of body 36 by support housing 12 helps to preclude failure of body 36 by hydraulic forces applied to body 36 when filled with fluid.

Although in the above discussed embodiment container 32 has a flexible, bag-like configuration, in alternative embodiments it is appreciated that container 32 can comprise any form of collapsible container or semi-rigid container. Furthermore, in contrast to having a closed top end wall 48, container 32 can comprise an open top liner. Container 14 can also be transparent or opaque and can have ultraviolet light inhibitors incorporated therein.

Mounted on top end wall 48 are a plurality of ports 52 which are in fluid communication with chamber 40. Although two ports 52 are shown, it is appreciated that one or three or more ports 52 can be present depending on the intended use of container 32. As such, each port 52 can serve a different purpose depending on the type processing to be undertaken. For example, ports 52 can be coupled with a tube 54 for dispensing fluid or other components into chamber 40 or withdrawing fluid from chamber 40. In addition, such as when container 32 is used as a bioreactor for growing cells or microorganisms, ports 52 can be used to provide various probes, such as temperature probes, pH probes, dissolved oxygen probes, and the like, access to chamber 40.

Extending through bottom end wall 50 of container 32 is a hole 60. Hole 60 is aligned with opening 24 on floor 22 of support housing 12. A portion of sparger 34 extends through hole 60 and opening 24. Sparger 34 is sealed to body 36 of container 32 so that fluid cannot leak out through hole 60. In general, sparger 34 comprises a base 62 having a flexible, gas permeable sparging sheet 64 mounted thereon.

Figure 2:
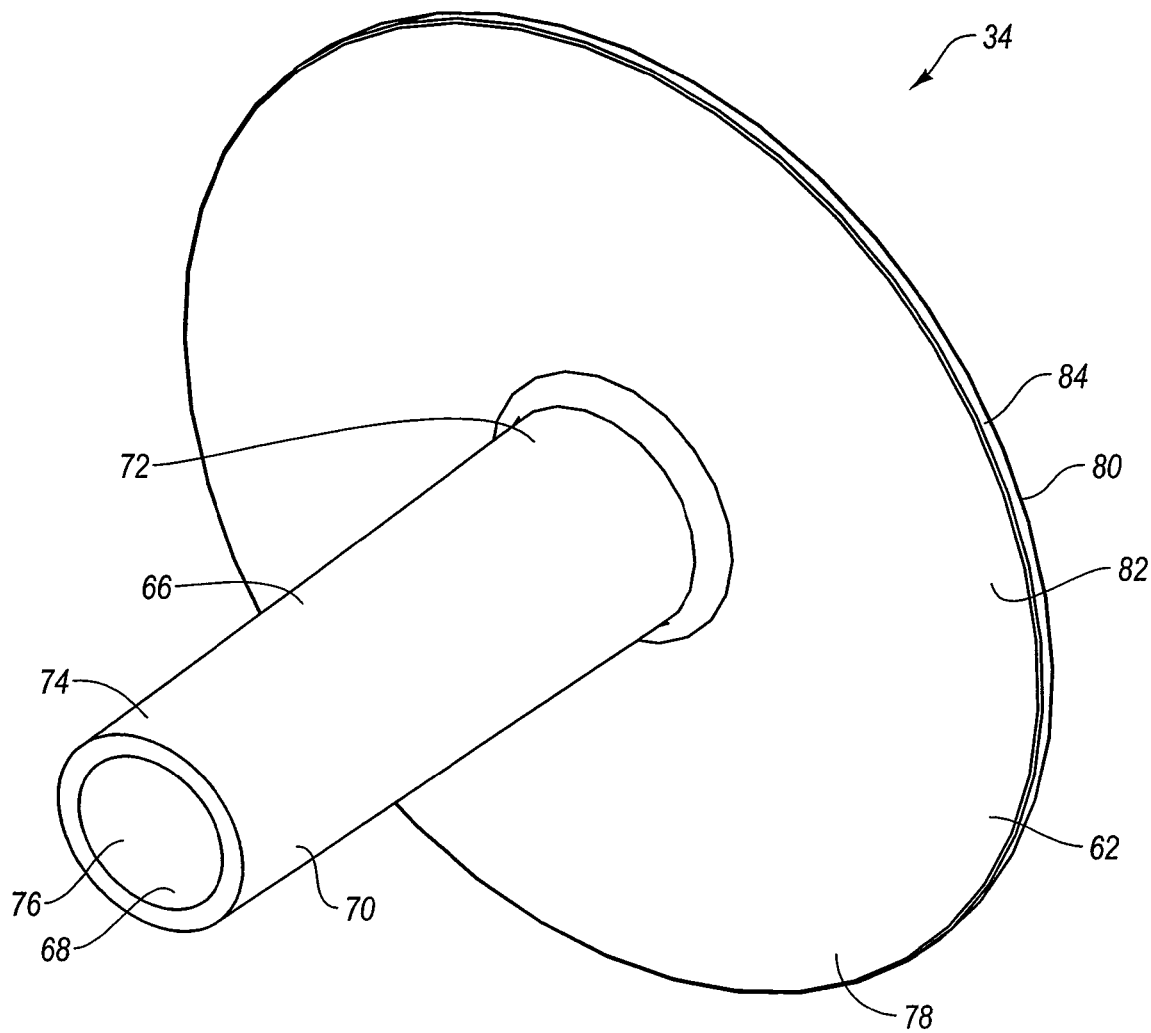
FIG. 2 is a bottom perspective view of the sparger of the containment system depicted in FIG. 1.

Turning to FIG. 2, base 62 of sparger 34 comprises a tubular member 66 having an interior surface 68 and an opposing exterior surface 70 each extending between a first end 72 and an opposing second end 74. Interior surface 68 bounds a passage 76 that longitudinally extends through tubular member 66. A flange 78 encircles tubular member 66 at first end 72 and radially outwardly projects therefrom. In the embodiment depicted, flange 78 has a substantially circular configuration. In alternative embodiments, flange 78 can be any other desired shape such as elliptical, square, or other polygonal or irregular configurations. Flange 78 has a first side 80 and an opposing second side 82 that each extend out to a perimeter edge 84. Tubular member 66 and flange 78 can be molded as a unitary integral piece. Alternatively, tubular member 66 can be connected to flange 78 by welding or other conventional techniques.

In one embodiment, base 62 is molded from a soft, resiliently flexible polymeric material or elastomeric material such as polyethylene, silicone or KRATON® having a durometer on a Shore A scale with a value of less than 90 and more preferably less than 70 but typically greater than 5. In other embodiments, other thermoset or thermoplastic polymers having a durometer in the above range can also be used. Other materials such as those previously discussed with regard to container 32 can also be used. In some embodiments, as a result of the material properties, tubular member 66 can be manually folded over so as to kink passage 76 closed or tubular member 66 can be manually pinched to close passage 76 wherein in each case tubular member 66 will resiliently return to the original configuration with no permanent deformation.

In one embodiment, flange 78 has a maximum diameter typically in a range between about 2 cm to about 30 cm with about 5 cm to about 15 cm being more common. Tubular member 66 typically has a length in a range between about 2 cm to about 30 cm with about 5 cm to about 15 cm being more common. Likewise, tubular member 66 typically has a maximum inner diameter in a range between about 0.2 cm to about 5 cm with about 0.5 cm to about 3 cm being more common. In alternative embodiments, it is appreciated that each of the above dimensions can be varied. For example, if desired tubular member 66 can comprise an elongated tube having a length of one meter or longer. It is further noted that in the present embodiment second end 74 of tubular member 66 has a smooth, substantially cylindrical configuration on interior surface 68 and exterior surface 70 with no flanges, barbs, or other projections extending therefrom.

One of the benefits of base 62 is that it is more easily adaptable for coupling with tubes of different diameter or configuration. For example, it is envisioned that container system 30, which comprises container 32 and sparger 34, could be sold to an end user as a single unit. In turn, the established system of the end user may have a variety of different sizes or types of gas hoses that would connect with tubular member 66 of sparger 34 for delivering gas thereto. As a result of flexible tubular member 66, only a single coupler having opposing ends with predefined sizes is needed to couple tubular member 66 to the gas hose. For example, depicted in FIG. 1, a tubular coupler 88 is provided having opposing ends 90 and 92 with annular barbs radially outward projecting therefrom. First end 90 is secured within passage 76 at second end 74 of tubular member 66. Tubular member 66 resiliently constricts around coupler 88 to form a fluid tight seal therewith. A plastic pull tie 77 can also be secured around the portion of second end 74 of tubular member 66 disposed over coupler 88 so as to further secure the sealed engagement therebetween. Second end 92 of coupler 88 is received within a first end 94 of a gas line 96. If gas line 96 has a diameter different than tubular member 66, a standard coupler 88 can be provided with second end 92 having a size configured to couple with gas line 96.

In contrast, if a conventional barbed stem were formed on flange 78, it would be necessary to first couple a tube to the barbed stem and then use coupler 88 to account for the change in size of gas line 96. As a result, tubular member 66 provides for a more universal connection. Furthermore, as a result of flange 78 and tubular member 66 both being comprised of a soft and flexible material, container 32 can folded and/or rolled up for transport and/or storage without fear of damage to sparger 34 and/or container 32.

Figure 3:
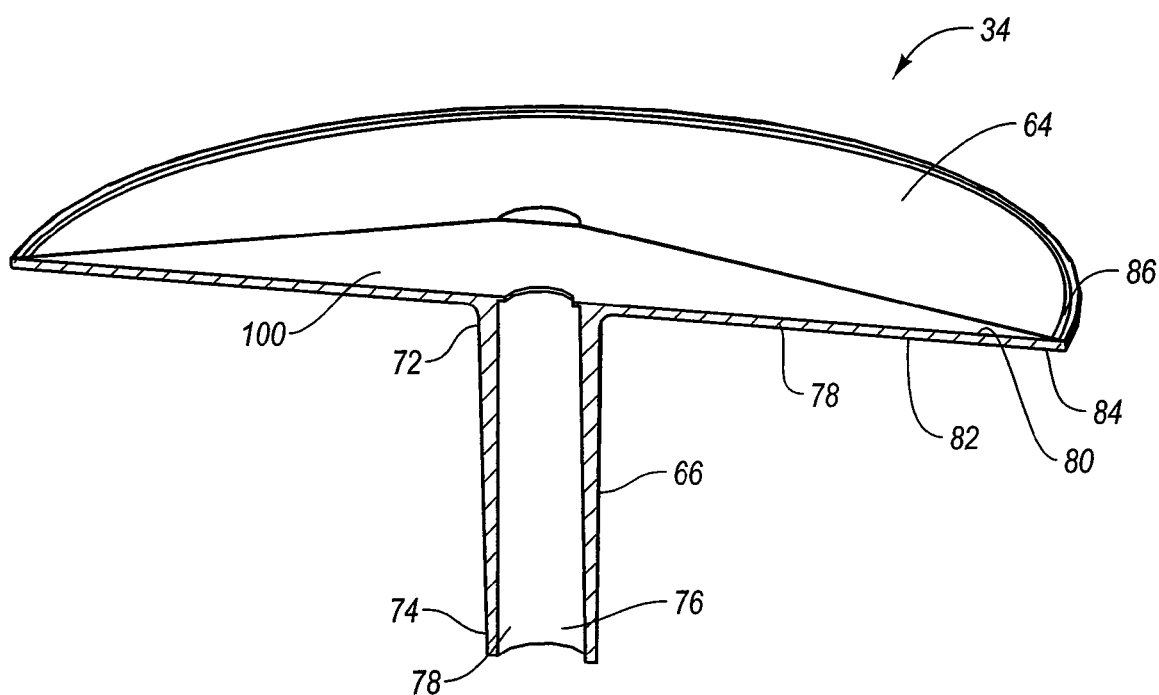
FIG. 3 is a cross sectional side view of the sparger show in FIG. 2.

Turning to FIG. 3, sparging sheet 64 is secured to first side 82 of flange 78 at or adjacent to perimeter edge 84 of flange 78. As a result, a compartment 100 is formed between first side 80 of flange 78 and sparging sheet 64. Passage 76 of tubular member 66 communicates with compartment 100. In the depicted embodiment, sparging sheet 64 has substantially the same configuration as flange 78. In alternative embodiments, sparging sheet 64 can have a configuration different than flange 78. For example, where flange 78 remains circular, sparging sheet 64 can be elliptical, square, triangular, or have other polygonal or irregular configurations. Furthermore, sparging sheet 64 need not extend all the way out to perimeter edge 84 but can be secured to flange 78 at a location radially spaced inward from perimeter edge 84. In this design, flange 78 includes an annular edge portion that extends between the edge of sparging sheet 64 and perimeter edge 84. This edge portion can be used for sealing flange 78 to container 32. It is also appreciated that sparging sheet 64 can be configured to rest flat against flange 78 or can be configured to tent upward when compartment 100 is filled with gas. By increasing the surface area of sparging sheet 64, sparging can be accomplished over a greater area.

In one embodiment sparging sheet 64 can be secured to flange 78 by directly welding the perimeter edge 86 of sparging sheet 64 to flange 78. Depending on the type of material used for sparging sheet 64 and flange 78, conventional welding techniques such as heat welding, RF energy, ultrasonic, and the like can be used. In still other embodiments, various forms of adhesives can be used to connect sparging sheet 64 to flange 78. In addition, there are numerous forms of mechanical type fasteners that can be used to form the connection. For example, one or more crimps or clamps can be used to secure sparing sheet 64 to flange 78. Other conventional fastening techniques can also be used.

Figure 3A:
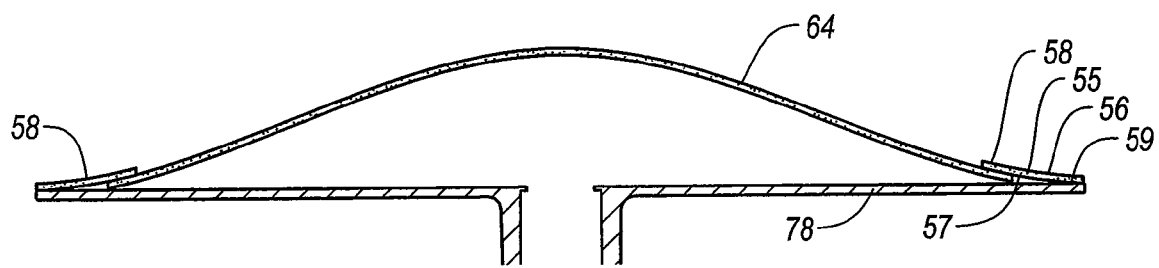
FIG. 3A is a cross sectional side view of the sparger shown in FIG. 3 using a transition member to connect the base to the sparging sheet.
Figure 3B:
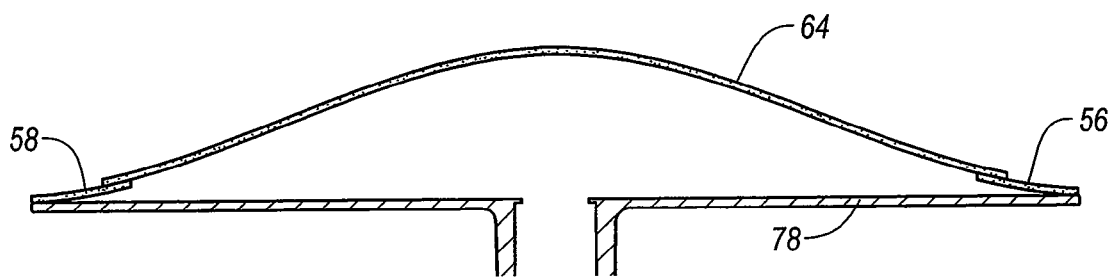
FIG. 3B is a cross sectional side view of the sparger shown in FIG. 3A showing a modified connection using the transition member.

In contrast to securing sparging sheet 64 directly to flange 78, a transition member can be used therebetween. For example, depicted in FIG. 3A, a ring shaped transition member 55 has a top surface 56 and an opposing bottom surface 57 extending between an inside first end 58 and an outside second end 59. Transition member 55 is typically formed from a sheet of polymeric material that will easily and securely bond with flange 78 by any of the welding techniques previously discussed. Examples of such materials include the same materials as previously discussed with regard to base 62 and body 36. During assembly, bottom surface 57 at second end 59 of transition member 55 is welded to flange 78. First end 58 is not secured to flange 78 and is thus free to move relative thereto. Sparging sheet 64 is secured to transition member 55 such as by being welded to bottom surface 57 at first end 58 (FIG. 3A) or by being welded to top surface 56 at first end 58 (FIG. 3B).

Depending on the type of material used for sparging sheet 64, using transition member 55 can produce a number of benefits. For example, as will be discussed below in greater detail, one type of material that can be used for sparging sheet 64 is a spun-bonded olefin material such as that commonly sold under the tradename TYVEK®. However, heat welding a non-coated spun-bonded olefin material to flange 78 can cause the spun-bonded olefin material to thin, thereby decreasing its structural strength. When gas is applied to sparger 34, a high stress, point load is formed at the inside intersection between sparging sheet 64 and flange 78. Depending on the amount of thinning of sparging sheet 64, this load can result in failure of sparging sheet 64. By using transition member 55, the high stress, point load caused by the gas is formed between flange 78 and transition member 55 which, due to material compatibilities, can easily withstand the load without failure. By welding sparging sheet 64 onto the freely movable first end 58 of transition member 55, the load between sparing sheet 64 and transition member 55 is uniformly applied in shear across the weld between the two members. This decreased load can be easily handled by sparging sheet 64 even after thinning.

Figure 3C:
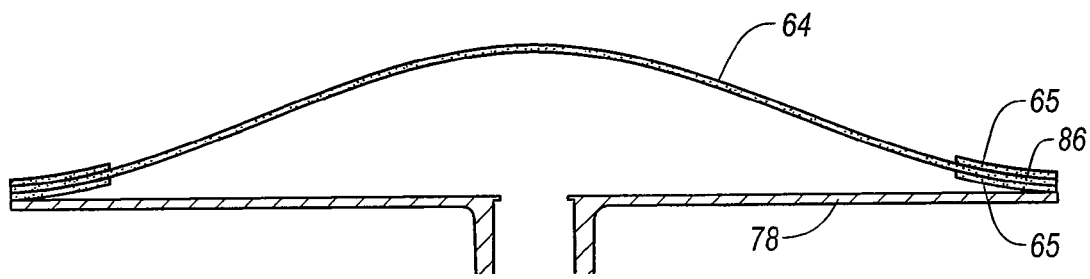
FIG. 3C is a cross sectional side view of the sparger shown in FIG. 3 wherein the perimeter edge of the sparging sheet has a polymeric coating and is connected to the base.

In another alternative embodiment as depicted in FIG. 3C, a coating 65 can be applied on one or both sides of perimeter edge 68 of sparging sheet 64. Coating 65 can comprise a polymeric material, such as low-density polyethylene, ethylene vinyl acetate or other coatings commonly used to coat TYVEK®. Coating 65 can minimize or prevent thinning of sparging sheet 64 so that the coated portion of sparing sheet 64 can be directly welded to flange 78.

Sparging sheet 64 can be comprised of a variety of different materials having a variety of different properties. As previously discussed, sparging sheet 64 is typically comprised of a sheet of gas permeable flexible material. Sparging sheet 64 typically has a thickness in a range between about 20 µm to about 2.5 cm, with about 20 µm to about 5000 µm being common, about 20 µm to about 1,000 µm being more common, and 50 µm to about 300 µm being still more common. Sparging sheet 64 can also have a burst strength in a range between about 2 psig (14 kPa) to about 50 psig (343 kPa), with about 2 psig (14 kPa) to about 25 psig (172 kPa) being more common, and about 2 psig (14 kPa) to about 10 psig (68 kPa) being even more common. Sparging sheet 64 can also be produced having a porosity in a range between about 0.1 to about 300 (sec/100 cc $IN^2$), with about 5 to about 100 (sec/100 cc $IN^2$) being common, 5 to about 60 (sec/100 cc $IN^2$) being more common, and about 5 to about 30 (sec/100 cc $IN^2$) being still more common as measured using the quantitative property of Gurley Hill Porosity. Such thicknesses, burst strength, and porosity can vary and depend in large part on the type of material being used.

In some embodiments, sparging sheet 64 is comprised of a material that is both vapor-permeable and water-resistant. That is, although the gas can pass through sparging sheet 64, water and some other fluids are prevented from flowing therethrough when not in use. Similarly, sparging sheet 64 may be constructed so as to only allow gas to pass therethrough when it is subject to sufficiently high gas pressure. It is often desirable to have a material with high permeability while maintaining hydrophobicity, strength, weldability, biocompatibility, and gamma stability.

It is also often desirable to have a flexible material that welds readily to common materials used in conventional ports and films (such as films discussed with regard to container 32). For example, the flexible nature of a soft or paper like film can allow it to be folded during manufacturing, packaging, loading, and use of the bioreactor. It may also be desirous to allow for the surface area and shape of the sparge material to easily be modified or changed according to weld or cut pattern.

Examples of select types of materials that can be used in the formation of sparging sheet 64 include: (1) polymeric nonwoven fabrics, (2) solvent cast polymeric films, (3) open cell foamed polymer sheets, and (4) perforated polymeric sheets. As used herein, the term "nonwoven fabric" means a web having a structure of individual fibers or threads that are interlaid, but not in an identifiable manner such as in knitted or woven fabric. Nonwoven fabrics can be formed by many processes such as for example, meltblowing processes, spunbonding processes, hydroentangling, air-laid and bonded carded web processing. One specific type of nonwoven fabric that has been found particularly useful in the present invention is spun-bonded olefin materials that are commonly sold under the tradename TYVEK®. TYVEK® is typically formed by a process using continuous and very fine fibers that are comprised of a high-density polyethylene. The fibers typically having an average diameter in a range between about 2 micrometers to about 8 micrometers. These fibers are flash-spun and then laid as a web on a moving belt in a randomly distributed and nondirectional pattern. Finally, the web of fibers are bonded together using heat and pressure. The final web typically has a thickness in a range between about 50 microns to about 250 microns.

TYVEK® has been found useful in view of its favorable qualities of having high permeability while maintaining hydrophobicity, strength, weldability, biocompatibility, and gamma stability. TYVEK® film can be produced having a porosity in a range between about 6 to about 30 (sec/100 cc $IN^2$) as measured using the quantitative property of Gurley Hill Porosity. Permeability rated according to the methods of Bendtsen Air Permeability are often in a range between about 400 to about 2000 (ml/min). Medical grades of TYVEK® typically have a relative pore size of about 20 (micrometers) and a surface energy of about 25 to about 32 (dynes/cm). Moisture Vapor Transmission Rates (MTVR) often ranges from about 1500 to about 1640 ($g/m^2$/24 hrs).

As used herein, the term "solvent cast polymeric films" means polymeric films that are initially produced with a solvent. The solvent is removed during the production process so that the resulting film has a desired porosity. Examples of cast polymeric films include polytetrafluoroethylene sold under the tradename TEFLON®, polysulfone, polypropylene, silicone, KYNAR® (PVDF), GORTEX® and the like. In one embodiment, the cast polymeric films can be attached is a porous support layer such as a woven fabric or one of the other materials described herein.

Open cell foamed polymer sheets are well known in the art and can be formed from a variety of different polymeric materials such as low density polyethylene, high density polyethylene, polypropylene, or polyurethane. The materials are foamed with a gas using conventional processes to form an open cell structure that is porous to gas. It is envisioned that open cell foamed polymer sheets will typically have a thickness in a range between about 1 mm to about 25 mm.

Perforated polymeric sheets include sheets of polymeric material that are formed using conventional processes, such as extrusion, and are then subsequently perforated so as to make the sheet porous. The small perforated holes can be produced such as by being punched or embossed into the sheet. In one embodiment the perforated holes can have a diameter in a range between about 20 μm to about 5 mm with about 20 μm to about 500 μm being more common. Perforated polymeric sheets can be produced from a variety of different materials such as polyethylene, different fluorinated polymers and other materials as previously discussed with regard to body 36.

In some embodiments, sparging sheet 64 can include a combination or laminate of two or more of the above types of materials.

Returning to FIG. 1, bottom surface 82 of flange 78 is sealed to bottom end wall 50 of container 32 so as to secure sparger 34 to container 32 and to prevent liquid from leaking out through hole 60. Flange 78 is typically secured to container 32 by conventional welding techniques. Alternatively, however, adhesives or mechanical connections can also be used. During the assembly stage, sparging sheet 64 and container 32 can be secured to opposing sides of flange 78 either simultaneously, such as through a welding process, or in progressive stages in any desired order. Once container system 30 is fully assembled, the system can be sealed within a storage bag and then the entire system sterilized such a through various forms of radiation sterilization.

During operation, container system 30 is positioned within compartment 20 of support housing 12 so that tubular member 66 of sparger 34 passes down through opening 24 in floor 22 of support housing 12. Gas line 96 is then coupled with tubular member 66 using coupler 88 as previously discussed. In alternative embodiments, tubular member 66 can be formed as an elongated tube which can extend directly to the gas source.

Next, a fluid 104 is dispensed into chamber 40 of container 32 by way of port 52. Fluid 104 can comprise a variety of different materials. For example, where container system 30 is being used as a bioreactor for growing cells or microorganisms, fluid 104 can comprise a growth media that is dependent upon the type of cells or microorganism being cultured. The fluid can also include a seed inoculum such as bacteria, fungi, algae, plant cells, animal cells, protozoans, nematodes, or the like. The present invention can also be used for non-biological systems. For example, the system can be used for processing or mixing solutions where it is desired to control or regulate the pH or partial pressure of gas within a solution.

Once fluid 104 is disposed within chamber 40 of container 32 and/or simultaneously with the filling thereof, a gas can be delivered through gas line 96 so as to enter compartment 100 of sparger 34. The gas migrates through sparging sheet 64 where it then contacts fluid 104 within chamber 40. Because of the relatively large surface area of sparging sheet 64 and the small pore size thereof, the gas passes out through sparging sheet 64 in the form of microbubble that can be easily entrained within fluid 104. Again, the type of gas passing through sparger 34 depends upon the type of processing needed for the fluid within chamber 40. Where cells are microorganisms are being cultured, the gas typically comprises air that is selectively combined with oxygen, carbon dioxide, and/or nitrogen. Again, in other embodiments specific gases, such as those identified above, or combinations of gases can be passed through sparger 34.

As also depicted in FIG. 1, in one embodiment it may be beneficial to use a check valve 106 along gas line 96 or at sparger 34 to reduce undesirable transfer of fluid vapor through sparging sheet 64 when sparger 34 is submerged and not in use. Actual moisture transmission rates may vary largely with the type of fluid 104 used and the particular application.

Although not required, in one embodiment means are provided for mixing fluid 104 within chamber 40. By way of example and not by limitation, in one embodiment a drive shaft 110 projects into chamber 40 and has an impeller 112 mounted on the end thereof. External rotation of drive shaft 110 thus facilitates rotation of impeller 112 which mixes and/or suspends fluid 104 within chamber 40. Sparger 34 is typically disposed directly below the means for mixing such that the mixing or movement of fluid 104 produced by the mixer helps to entrain the gas bubbles within fluid 104. One specific example of how to incorporate a rotational mixer into a flexible container is disclosed in U.S. Patent Publication No. US 2005/0239199 A1 published Oct. 27, 2005 which is incorporated herein by specific reference. Another example is disclosed in U.S. Provisional Patent Application filed Mar. 20, 2006, entitled Mixing Systems and Related Mixers in the names of Whitt F. Woods et al. which is incorporated herein by specific reference.

Figure 4:
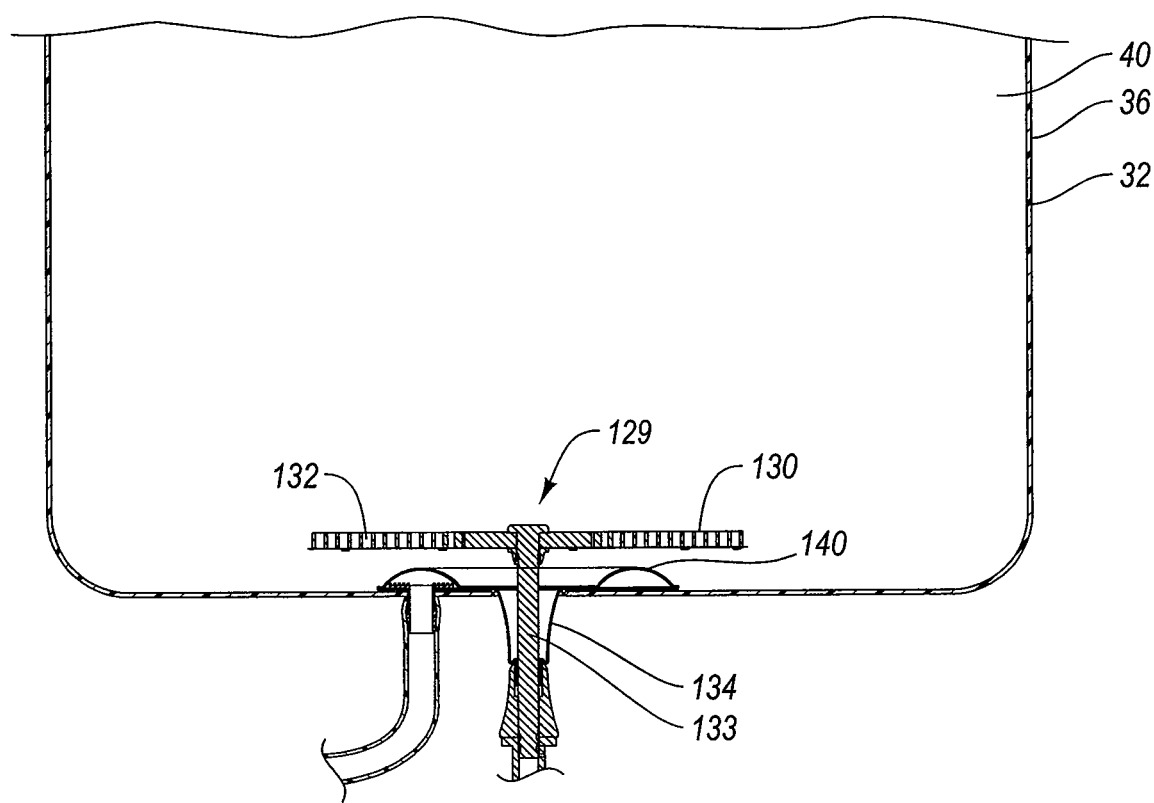
FIG. 4 is a cross section side view of the container shown in FIG. 1 having a vertical mixer disposed therein.
Figure 5:
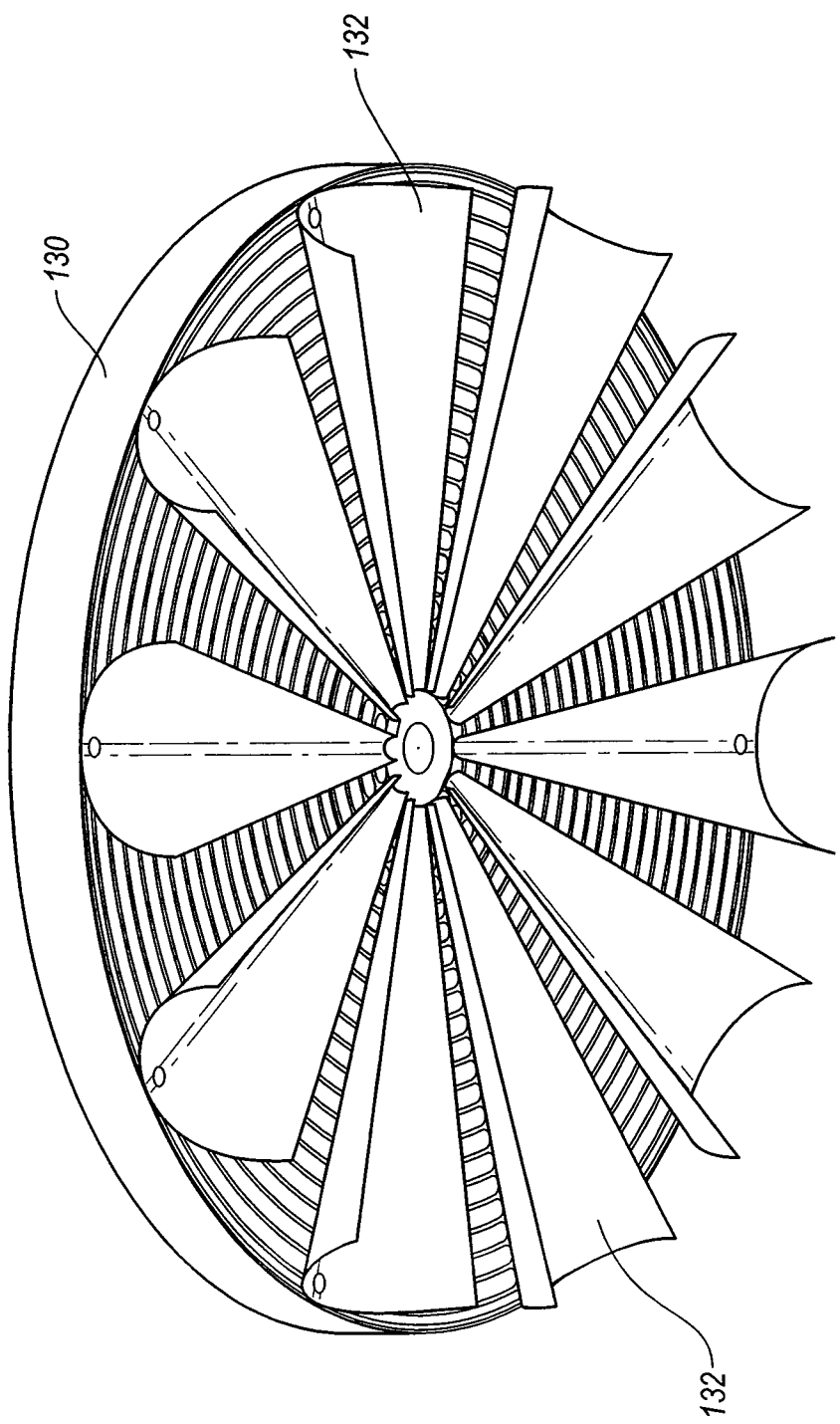
FIG. 5 is a bottom perspective view of the mixing disk of the vertical mixer shown in FIG. 4.

In an alternative embodiment of the means for mixing, mixing can be accomplished by vertically reciprocally moving a vertical mixer within chamber 40. For example, depicted in FIG. 4 is one embodiment of a vertical mixer 129 comprising a mixing disk 130 have a plurality of openings 131 extending therethrough. As depicted in FIG. 5, a plurality of flexible flaps 132 are mounted on the bottom surface of mixing disk 130 such that as disk 130 is moved vertically upward, flaps 132 open to allow the fluid to pass through openings 131 and when disk 130 is pulled downward, flaps 132 lay flush against disk 130, thereby closing openings 131. With openings 131 closed, mixing disk 130 forces the fluid down and then back up and around mixing disk 130 so as to mix the fluid within container 32.

A shaft 133 extends down mixing disk 130 and passes out through an opening in container 32. Outside of container 32, shaft 133 connects with a drive mechanism for selectively raising and lower shaft 133 at a desired frequency and over a desired height. A flexible diaphragm 134 extends between container 32 and shaft 133 so as to form a sealed fluid connection between shaft 133 and container 32. As shaft 133 raises and lowers, flexible diaphragm 134 flexes to allow free movement of shaft 133 and thus mixing disk 130. Further disclosure with regard to the assembly and operation of vertical mixer 129 is disclosed in U.S. patent application Ser. No. 11/127,651, filed May 11, 2005 which is incorporated herein by specific reference. In yet other embodiments, it is appreciated that the mixing can be accomplished by simply circulating fluid through chamber 40 such as by using a peristaltic pump to move fluid in and out of chamber 40. Other conventional mixing techniques can also be used.

Welding sparger 34 onto container 32 can provide for a high level of surface area while providing a low-profile sparge. In some embodiments, this can reduce turbulence near impeller 112 and/or reduce the possibility of cells accumulating in cracks, seams, or crevices. Furthermore, using a single use disposable container system 30 may be helpful in avoiding or reducing contamination and cleaning issues that may be associated with some conventional spargers, which sometimes involve cleaning numerous holes, pores, and crevices of such units. For example, small void areas in some spargers may present areas for cell debris or other material to lodge and accumulate leading to increased occurrence of contamination. In some cases, this may carry over in subsequent runs.

As previously discussed, one purpose of using sparger 34 in a cell culture is to aid in the mass transfer of oxygen (kLa), which is often necessary for the respiration of the growing cells. An advantage of using sparger 34 in a single use bioreactor is that the tortuous pore structure of sparging sheet 64, such as when TYVEK® is used, can allow for a beneficial effect on mass transfer of oxygen from the bulk gas introduced through sparger 34. In some embodiments, it is desirable to have small bubbles introduced into the bioreactor as they can benefit mass transfer. Mass transfer across a permeable membrane can occur independent of mass transfer resulting from a gas bubble. Relatedly, a long gas retention time within the fluid column and a higher surface to volume ratios are often desirable effects.

It is generally accepted that the bubble size can be dominated by surface tension effects, inherently related to the component ratio of salts, proteins, sugars, and micro and macro components of the nutrient media. Experimentally calculated kLa values, visual observation, and data from bioreactor runs often indicate that bubble size and perhaps improved mass transfer are qualities of the present sparge approaches. The composition and rheological properties of the liquid, mixing intensity, turnover rate of the fluid, bubble size, presence of cell clumping, and interfacial absorption characteristics all influence mass transfer of gas such as oxygen to the cells. Main driving forces of mass transfer include surface area and concentration gradient. In many cases, a main source of resistance of oxygen mass transfer in a stirred tank bioreactor can be the liquid film surrounding the gas bubble.

By using TYVEK® and the other similar gas permeable membranes as discussed above, the surface area of sparging sheet 64 can easily be increased. In some embodiments, the oxygen gradient between sparging sheet 64 and the liquid interface can be maintained at a high level through constant replenishment directly through a sparge inlet. Further, a rapid mixing intensity can also benefit mass transfer as the impeller 112 pumps media directly down onto sparging sheet 64. The use of a gas permeable membrane can allow for mass transfer of oxygen across the bulk film surface, which can be in addition to the formation of bubbles that rise within the fluid column.

In many cases, small bubbles can lead to greater foaming at the top of a bioreactor, which can have negative effects on cell viability and kLa according to Henry's law and the solubility of gases related to partial pressures. This boundary layer often results in a reduced ability to control dissolved oxygen levels within the bulk liquid. Typically, it is desirable to avoid or mitigate the presence of foam, as excessive amounts can result in exhaust filter blocking and run failure. The novel sparger approaches described herein can provide the desired mass transfer properties, often with reduced levels of foam generated as compared to conventional systems. This may be due to greater efficacy and less gas being introduced through the sparger to maintain a target oxygen solubility.

Figure 6:
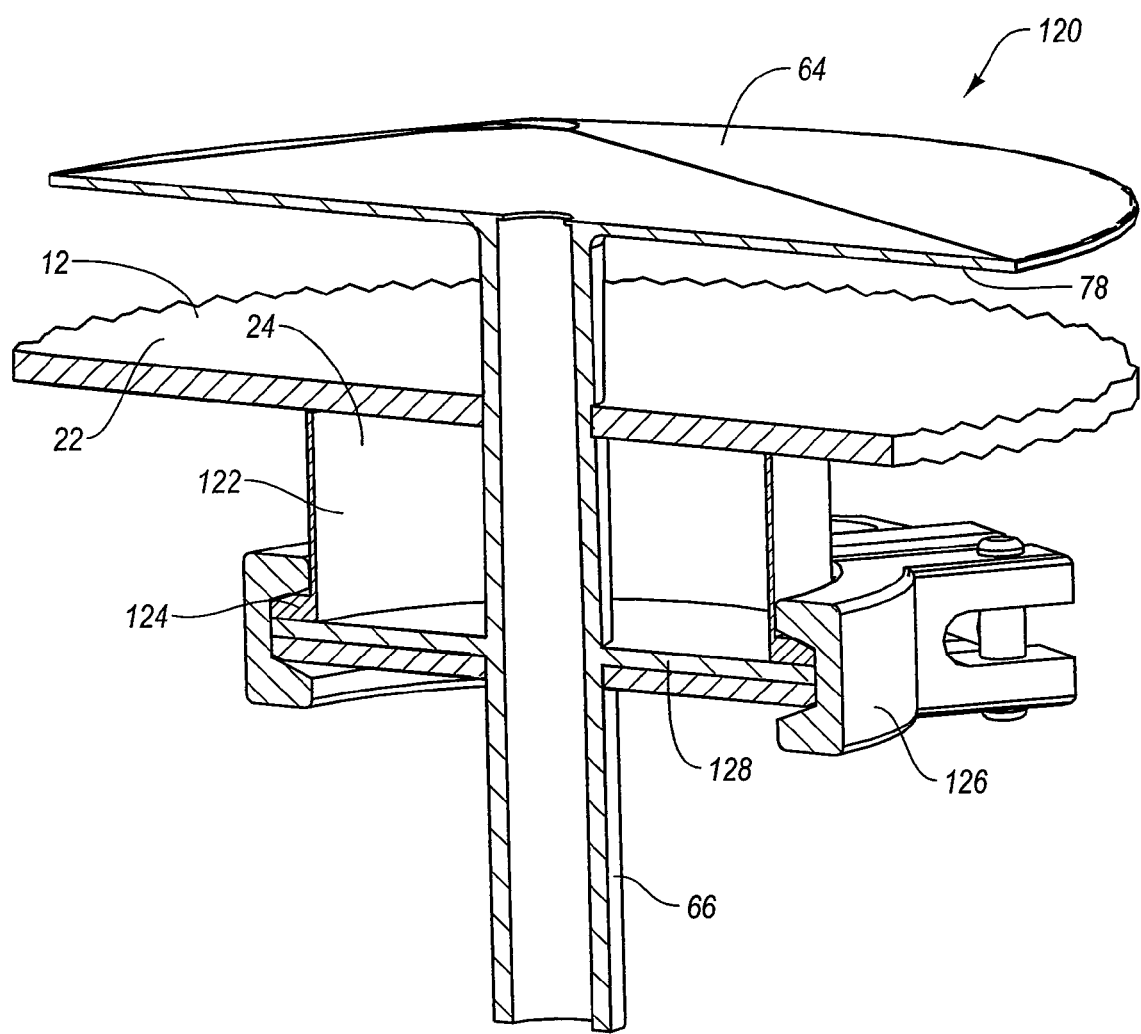
FIG. 6 is a cross sectional side view of an alternative embodiment of a sparger mounted on a rigid support housing.

It is appreciated that sparger 34 can come in a variety of different sizes, shapes, designs, and configurations. By way of example and not by limitation, depicted in FIG. 6 is an alternative embodiment of a sparger 120 incorporating features of the present invention. Like elements between sparger 120 and sparger 34 are identified by like reference characters. Previously discussed sparger 34 was disclosed as being mounted on flexible container 32. In contrast, sparger 120 is specifically designed to be removably mounted to a rigid container that is designed to hold fluid 104 without the use of a bag or liner. Specifically, as shown in FIG. 6, floor 22 of support housing 12 is shown having opening 24 extending therethrough. In this embodiment, however, a tubular collar 122 encircles opening 23 and extends down from floor 22. Collar 122 terminates at an annular lip 124.

Sparger 120 is substantially identical to sparger 34 except that tubular member 66 has been lengthened and a flange 128 encircles tubular member 66 and radially outward projects therefrom at a location between the opposing ends of tubular member 66. Flange has an outer diameter substantially the same as the outer diameter of lip 124 such that by positioning flange 128 against annular lip 124, a clamp 126 can secure flange 128 to annular lip 124, thereby sealing opening 24 closed. In this embodiment, fluid 104 can be dispensed directly into compartment 20 of support housing 12 and sparger 120 can be used to sparge fluid 104 therein. In view of the foregoing, sparger 120 can be retrofitted into existing rigid containers where the container is cleaned and sterilized between uses. However, sparger 120 remains a single use item that can be disposed of after each use.

Figure 7:
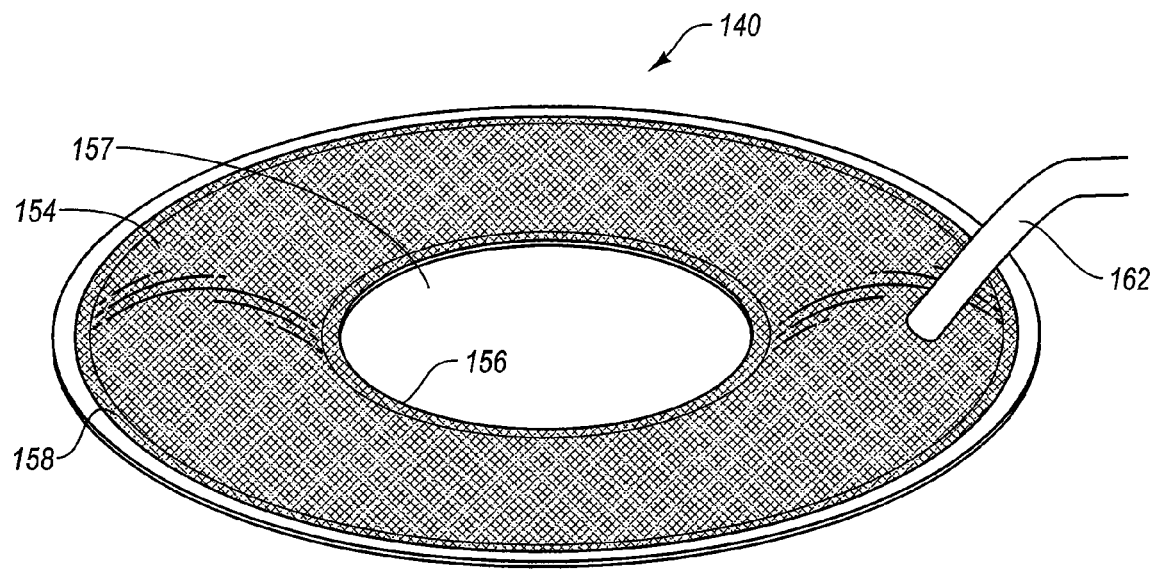
FIG. 7 is a top perspective view of an alternative embodiment of a sparger having a substantially donut shape configuration.
Figure 8:
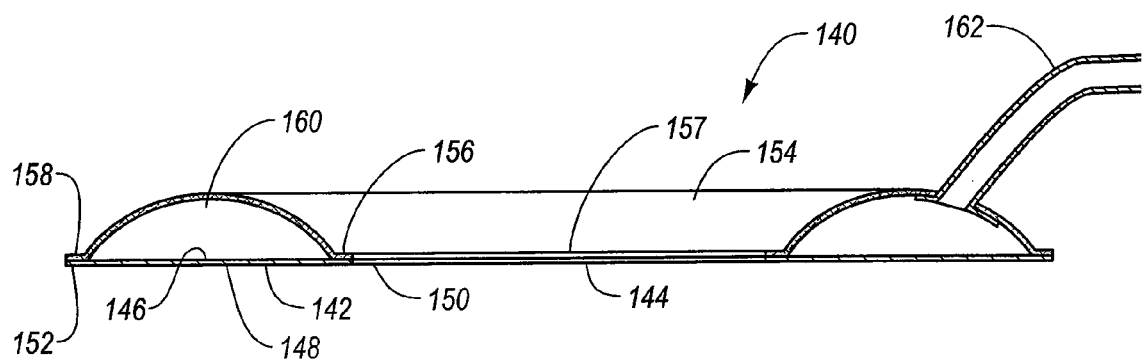
FIG. 8 is a cross sectional side view of the sparger shown in FIG. 5.

Depicted in FIGS. 7 and 8 is another alternative embodiment of a sparger 140 having a substantially ring or donut shape. Sparger 140 comprises a substantially circular base 142 having a hole 144 centrally extending therethrough. In one embodiment, base 142 comprises a flexible sheet of nonporous polymeric material such as an extruded sheet of polyurethane or polyethylene. Base 142 can be comprised of the same materials as previously discussed with regard to body 36. In an alternative embodiment, base 142 can comprise a semi rigid or substantially rigid plate. For example, base 142 can be comprised of a high density polyethylene material or other rigid type plastics. Base 142 includes a top surface 146 and an opposing bottom surface 148 each extending between an inside edge 150 and an opposing outside edge 152. Inside edge 150 bounds opening 144.

In the embodiment depicted, a substantially circular sparging sheet 154 is provided having an inside edge 156 that bounds a central opening 157 and an outside edge 158. Inside edges 150 and 156 and outside edges 152 and 158 are sealed together, respectively, using previously discussed techniques such as welding, adhesive, or mechanical fastener. As a result, a compartment 160 is formed between base 142 and sparging sheet 154. Sparging sheet 154 can have the same properties as previously discussed with regard to sparging sheet 64. Furthermore, in this embodiment and all other embodiments discussed herein, one or more transition members 55 can be used to connect the sparging sheets to a separate structure such as base 142.

A tube 162 is coupled with sparging sheet 154. Tube 162 can be selectively coupled with a gas source for delivering the gas to compartment 160. Sparger 140 can be secured to a container such as by being welded or otherwise secured to bottom end wall 50 of container 32. For example inner edge 150 and/or outer edge 152 can be welded or otherwise secured to container 32.

Alternatively, sparger 140 can simply be positioned on the floor of container 32 or on the floor of support housing 12. Sparger 140 can be held in place by being weighted or other removable fastening techniques can be used to secure sparger 140 in place. With sparger 140 positioned in place, tube 162 can extend out through one of ports 52. Alternatively, tube 162 can be coupled with base 142 and then extend out through a hole in the bottom of container 32 and/or support housing 12. In alternative modifications to sparger 140, hole 144 can be eliminated on base 142 and/or hole 157 can be eliminated on sparging sheet 154. In yet another modification, base 142 can be made of the same material as sparging sheet 154.

Figure 9:
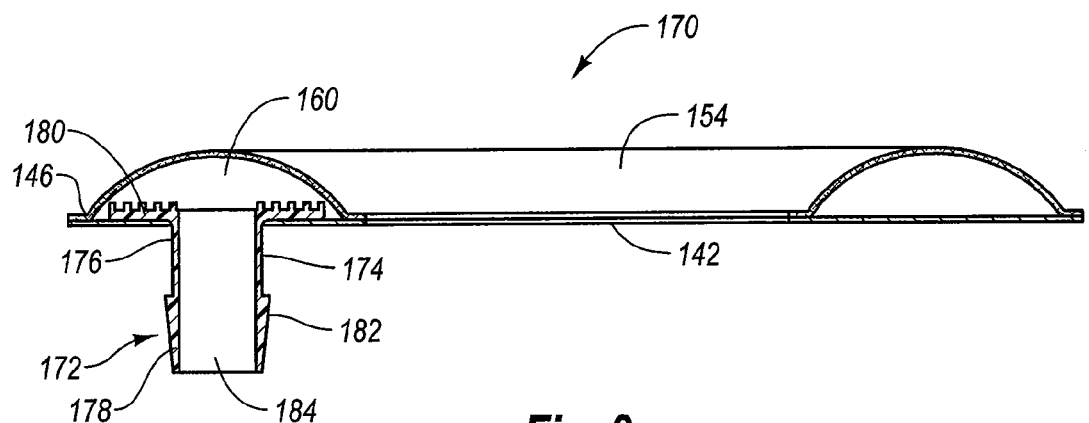
FIG. 9 is an alternative embodiment of the sparger shown in FIG. 6 wherein the tube has been replaced with a port that extends down through the base of the sparger.

Depicted in FIG. 9 is another alternative embodiment of a sparger 170. Like elements between sparger 170 and 140 are identified by like reference characters. Sparger 170 is substantially the same as sparger 140 and includes base 142 and sparging sheet 154. In contrast to sparger 140, however, in sparger 170 tube 162 has been removed and replace with a port 172 mounted on base 142. Port 172 comprises a stem 174 having a first end 176 and an opposing second end 178. Stem 174 is one form of a tubular member and bounds a passage 184 extending therethrough. A flange 180 encircles and radially outwardly projects from first end 176 of stem 174. Flange 180 is mounted to top surface 146 of base 142 such as by welding, adhesive, or other conventional techniques. Stem 174 extends down through a hole formed on base 142. A barb 182 encircles and radially outwardly projects from second end 178 of stem 174. Stem 174 is adapted to couple with a tube for delivering gas to compartment 160. During assembly, stem 172 can pass down through a hole formed in container 32 and/or support housing 12. The same modifications and mountings as previously discussed with regard to sparger 140 can also be implemented with sparger 170. In still a further embodiment, port 172 can be replaced with base 62 of sparger 34. In this regard, base 62 can be referred to and function as a port.

Figure 10:
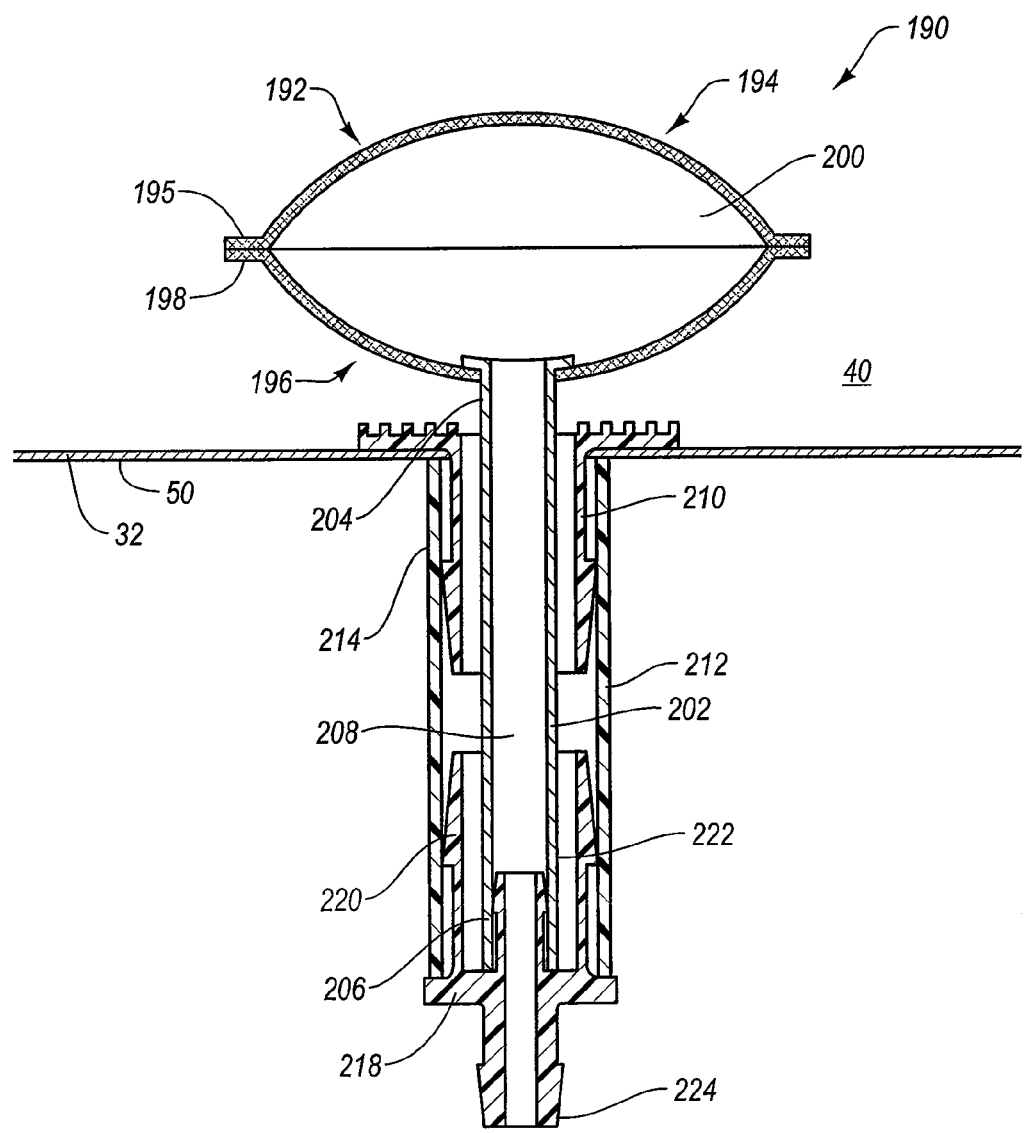
FIG. 10 is a cross sectional side view of another alternative embodiment of a sparger formed from a plurality of sparging sheets that are seamed together.

Depicted in FIG. 10 is another alternative embodiment of a sparger 190. Sparger 190 comprises a body 192 that includes a plurality of sparging sheets secured together. Specifically, body 192 includes a first sparging sheet 194 having a substantially circular configuration that terminates at a perimeter edge 195. Body 192 also includes a second sparging sheet 196 that also has a substantially circular configuration and terminates at a perimeter edge 198. Perimeter edges 195 and 198 have been seamed together such as by welding, adhesive, or fastener. As a result, a compartment 200 is bounded between sparging sheets 194 and 196. In alternative embodiments, body 194 can be formed from one or three or more sheets of material using the same methods as previously discussed with regard to container 32. It is appreciated that body 194 can be configured in any of a variety of shapes, including spheres, cylinders, boxes, pyramids, irregular shapes, and the like, and may include any combination of permeable and non-permeable materials or surfaces.

Sparger 190 further comprises a tubular member 202 having a first end 204 coupled with second sparging sheet 196 and an opposing second end 206. Tubular member 202 bounds a passage 208 that communicates with compartment 200. It is appreciated that sparger 190 can be used with a reusable rigid container or a disposable flexible container. In the embodiment depicted, container 32 is depicted having a tubular port 210 mounted on bottom end wall 50. A coupling tube 212 has a first end 214 connected to port 210 and an opposing second end 216 connected a coupler 218. Coupler 218 includes an outside stem 220 that is received within second end 216 of coupling tube 212 so as to form a sealed engagement therewith, an inside stem 222 that is coupled with second end 206 of tubular member 202, and a distal stem 224 that is in fluid communication with inside stem 222 and is adapted to couple with a gas line. In this configuration, gas can be delivered to compartment 200 of sparger 190 by being passed through coupling tube 212 while maintaining compartment 40 of container 32 sealed closed. It is appreciated that there are a variety of different coupling techniques and couplers that can be used to coupler sparger 190 to container 32 so that a gas can be delivered to sparger 190.

Figure 11:
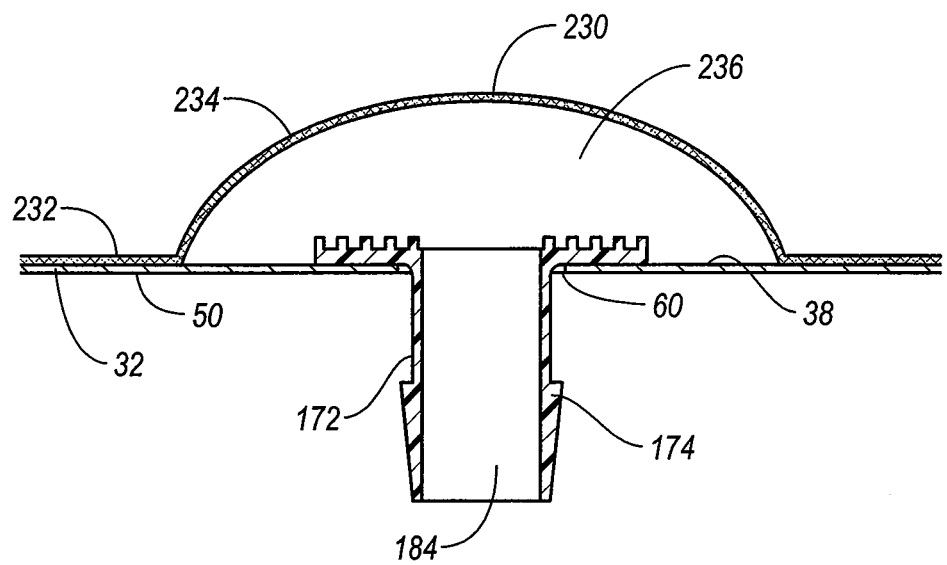
FIG. 11 is a cross sectional side view of an alternative embodiment of a sparger wherein a sparging sheet has been secured to a bottom end wall of a container.

Depicted in FIG. 11 is one embodiment of an inventive sparger 230 that is formed as a portion of container 32. Specifically, port 172, as depicted in FIG. 9, is mounted on interior surface 38 of bottom end wall 50 of container 32 so that stem 174 extends down through hole 60. Sparger 230 is formed by welding a perimeter edge 232 of a sparging sheet 234 directly to bottom end wall 50 of container 32 such that sparging sheet 324 encircles and covers port 172. As a result, sparger 230 has a compartment 236 that is bounded between bottom end wall 50 of container 32 and sparging sheet 234. As previously discussed, stem 174 of port 172 is adapted to couple with a gas line such that a gas can be delivered to compartment 236. It is appreciated that sparging sheet 234 as well as the other sparging sheets referenced herein can be made of the same alternative materials as previously discussed with regard to sparging sheet 64.

In the depicted embodiment, compartment 236 defines a dome-shaped space. Sparger assembly configurations such as those described herein can allow the surface area and corresponding gas flow rate requirements of, for example, sparging sheet 234, to be adjusted by utilizing different size shapes such as the dome shown here. As previously discussed, some embodiments of the present invention may include a check valve inline coupled with a tubing that is attached to port 172, which can prevent fluid backflow.

In alternative embodiments, port 172 can be replaced with base 62 as previously discussed with regard to FIG. 1. Alternative embodiments as previously discussed with regard to base 62 are also applicable to this alternative embodiment relating to FIG. 11. In this embodiment, flange 78 of base 62 can be directly secured to bottom end wall 50 of container 32 such that tubular member 66 extends through opening 60. Again, however, sparging sheet 234 attaches directly to bottom end wall 50 of container 32 without connecting directly to base 62.

In still other embodiments, it is appreciated that sparging sheet 234 and port 172 can be mounted at a variety of different location on container 32. In addition, sparging sheet 234 can be formed having any desired configuration. Port 172 can be replaced with a variety of alternative types of ports that can be used for coupling with a gas line and delivering a gas to compartment 236.

Figure 12:
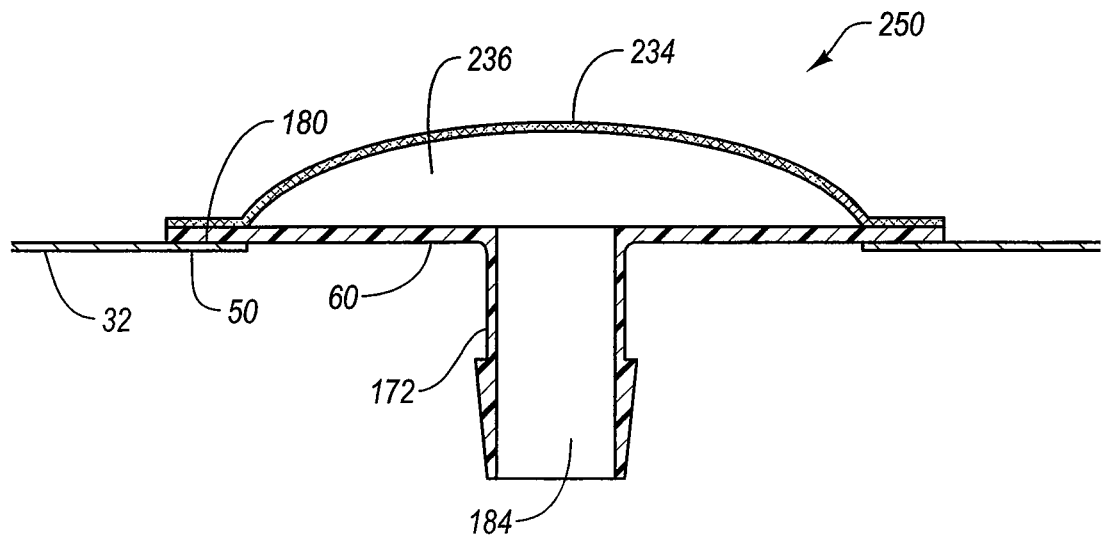
FIG. 12 is a cross sectional side view of another embodiment of a sparger wherein the sparging sheet has been secured to the flange of a port mounted on a container.

Depicted in FIG. 12 is another alternative embodiment of an inventive sparger 250. Sparger 250 is similar to sparger 230 and like elements are identified by like reference characters. In the embodiment depicted in FIG. 12, flange 180 of port 172 has been enlarged. Sparging sheet 234 has been secured directly to flange 180 so as to encircle and cover passage 184 extending through port 172.

Figure 13:
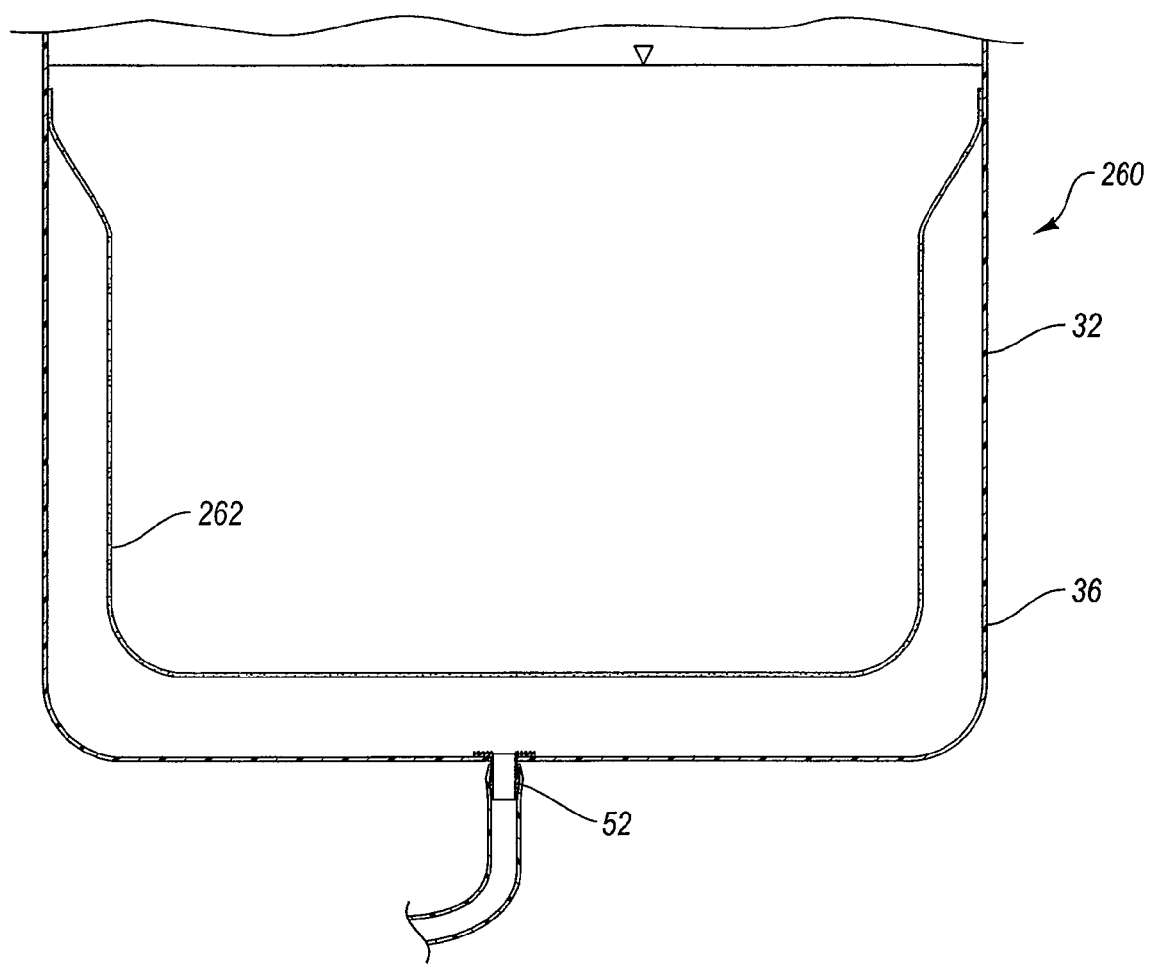
FIG. 13 is a cross sectional side view of a container system comprising a container having a sparging sheet as a liner.
Figure 14:
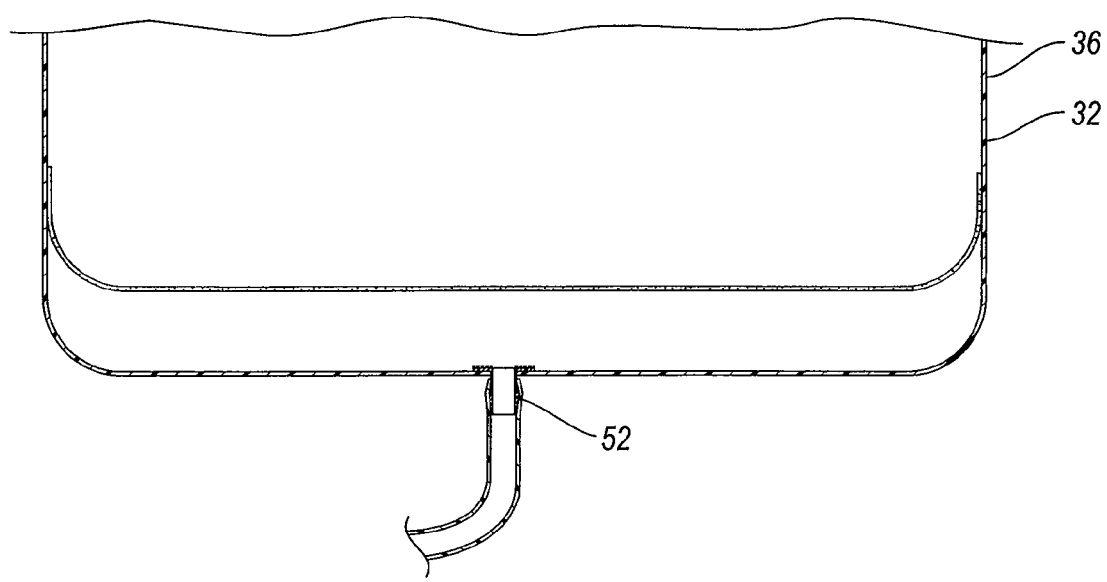
FIG. 14 is a cross sectional side view of a container system comprising a container having a sparging sheet lining a floor thereof.

Depicted in FIG. 13 is an alternative embodiment of a container system 260 incorporating features of the present invention. Container system 260 comprises container 32 that includes flexible body 36 having a port 52 mounted on the floor thereof. A flexible sparging sheet 262 is mounted to the sidewall of container 32 so as to cover at least a portion of the sidewall that extends below the fluid line and so as to also cover the floor of container. Sparging sheet 262 is formed from one or more of the porous materials previously discussed herein. During use, a gas is delivered through port 52. The gas permeates through sparging sheet 262 over a large surface area so that the gas can rapidly and efficiently be absorbed into the fluid. The embodiment depicted in FIG. 14 is substantially the same as that in FIG. 13 except that sparging sheet 262 only covers the floor of container 32.

The spargers of the present invention can also be used for the removal or stripping of undesirable dissolved compounds within the liquid. For example, a separate sparger, either used in conjunction or separately from the main sparger, can be used in a bioreactor to remove waste products created as a bioproduct of the biochemical reaction or cellular respiration (such as carbon dioxide). This sparger can be configured with larger pores in an effort to allow the undesirable dissolved gas components to be driven from the media in an effort to control variables such as pH, dissolved oxygen, or other process parameters.

It is appreciated that the foregoing embodiments are simply examples of alternative methods of forming spargers of the present invention. It is likewise appreciated that the various features of the different embodiments can be mixed and matched to produce still other embodiments.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A container system comprising:
    a bag comprised of one or more sheets of flexible polymeric material, the bag having an interior surface at least partially bounding a chamber, the chamber being adapted to hold a fluid;
    a sparger secured to the interior surface of the bag so that a compartment is formed between the interior surface of the bag and the sparger, at least a portion of the sparger being comprised of a sparging sheet comprised of a flexible sheet of a gas permeable material; and
    a tubular port or tube coupled with the bag so that a passage bounded by the tubular port or tube communicates with the compartment.

2. The container system as recited in claim 1, wherein the tubular port or the tube is spaced apart from the sparger.

3. The container system as recited in claim 1, wherein the sparger comprises the sparging sheet welded directly to the interior surface of the bag so that the compartment is formed between the interior surface of the bag and the sparging sheet.

4. The container system as recited in claim 3, wherein the welding between the sparging sheet and the interior surface of the bag encircles the tubular port or tube and is spaced apart from tubular port or tube.

5. The container system as recited in claim 1, wherein the sparger has a dome shaped configuration when the compartment is inflated with a gas.

6. The container system as recited in claim 1, wherein the bag has a floor with an encircling side wall upstanding therefrom, the sparger being secured to the floor of the bag and the tubular port or tube being secured to the floor of the bag.

7. The container system as recited in claim 1, wherein the bag has a floor with an encircling side wall upstanding therefrom, the sparger being secured to the encircling side wall of the bag and the tubular port or tube being secured to the floor of the bag.

8. The container system as recited in claim 1, wherein the bag comprises an open topped liner.

9. The container system as recited in claim 1, wherein the chamber of the bag is sterile.

10. The container system as recited in claim 1, further comprising a rigid support housing in which the bag is disposed.

11. The container system as recited in claim 1, further comprising a gas source coupled with the tubular port or tube.

12. The container system as recited in claim 1, wherein the sparging sheet is comprised of a nonwoven fabric, a solvent cast polymeric film, an open cell foamed polymer sheet, or a perforated polymer sheet.

13. The container system as recited in claim 1, wherein the tubular port is coupled with the bag, the tubular port comprising:
    an annular flange welded to the interior surface of the bag; and
    a tubular stem projecting from the flange and passing through an opening on the bag.

14. A method for sparging a fluid with a gas, the method comprising:
    dispensing a fluid into a chamber of a bag, a sparger being secured to an interior surface of the bag so that a compartment is formed between the interior surface of the bag and the sparger, at least a portion of the sparger being comprised of a sparging sheet comprised of a flexible sheet of a gas permeable material; and
    delivering a gas to the compartment so that the gas passes through the sparging sheet and into contact with the fluid in the chamber.

15. The method as recited in claim 14, wherein the step of dispensing the fluid comprises feeding one or more components into the chamber of the container to produce a liquid culture containing growing cells or microorganisms.

16. The method as recited in claim 15, wherein the gas is delivered containing a controlled level of oxygen so as to sparge the culture and maintain an oxygen partial pressure in the culture at levels suitable for the continued growth of the cells or microorganisms.

17. The method as recited in claim 14, wherein the gas is delivered containing a controlled level of oxygen or carbon so as to sparge the fluid and thereby adjust or regulate the pH or partial pressure of oxygen of the fluid.

18. The method as recited in claim 14, further comprising mixing the fluid within the chamber while the gas is delivered to the compartment.

19. The method as recited in claim 14, wherein the bag is comprised of one or more sheet of a flexible polymeric material, the method further comprising positioning the bag within a rigid support housing.

20. The method as recited in claim 14, wherein the sparger comprises the sparging sheet welded directly to the interior surface of the bag so that the compartment is formed between the interior surface of the bag and the sparging sheet.

21. The method as recited in claim 20, wherein the gas is delivered to the compartment through a tubular port or tube secured to the bag.

22. The method as recited in claim 21, wherein the bag has a floor with an encircling side wall upstanding therefrom, the sparging sheet being welded to the floor of the bag and the tubular port or tube being secured to the floor of the bag.

\* \* \* \* \*